US012575894B2

(12) United States Patent
Peter et al.

(10) Patent No.: US 12,575,894 B2
(45) Date of Patent: Mar. 17, 2026

(54) METHOD AND DEVICE FOR SEGMENTATION AND REGISTRATION OF AN ANATOMICAL STRUCTURE

(71) Applicant: GANYMED ROBOTICS, Paris (FR)

(72) Inventors: Loïc Peter, Zürich (CH); Nicolas Loy Rodas, Gennevilliers (FR); Marion Decrouez, Sèvres (FR)

(73) Assignee: GANYMED ROBOTICS, Paris (FR)

( * ) Notice: Subject to any disclaimer, the term of this patent is extended or adjusted under 35 U.S.C. 154(b) by 358 days.

(21) Appl. No.: 18/156,572

(22) Filed: Jan. 19, 2023

(65) Prior Publication Data

US 2023/0240762 A1      Aug. 3, 2023

(30) Foreign Application Priority Data

Jan. 19, 2022     (EP) ..................................... 22305056

(51) Int. Cl.
*A61B 34/20*          (2016.01)
*A61B 90/00*          (2016.01)

(52) U.S. Cl.
CPC .............. *A61B 34/20* (2016.02); *A61B 90/36* (2016.02); *A61B 2090/364* (2016.02)

(58) Field of Classification Search
CPC ... A61B 34/20; A61B 90/36; A61B 2090/364;
G06T 2207/10072; G06T 7/11; G06T 7/136; G06T 2207/10028; G06T 2207/30008; G06T 7/344
See application file for complete search history.

(56) References Cited

U.S. PATENT DOCUMENTS

2021/0059764 A1*   3/2021   Rafii-Tari .................. G06T 7/33
2021/0059766 A1*   3/2021   Graetzel ................ G16H 40/40
2024/0099777 A1*   3/2024   Moller ................... A61B 34/25

FOREIGN PATENT DOCUMENTS

WO          2020216934 A1    10/2020

OTHER PUBLICATIONS

Extended European Search Report dated Jul. 7, 2022 in corresponding European Patent Application No. 22305056.8, 4 pages.
Maier-Heinl et al., "Convergent Iterative Closest-Point Algorithm to Accomodate Anisotropic and Inhomogenous Localization Error", IEEE Transactions on Pattern Analysis and Machine Intelligence, IEEE Computer Society, USA, vol. 34, No. 8, Aug. 1, 2012, 13 pages.

* cited by examiner

*Primary Examiner* — Helen Zong
(74) *Attorney, Agent, or Firm* — Morgan, Lewis & Bockius LLP

(57)          ABSTRACT
A method and a device for segmentation of a preoperative model of a target anatomical structure in view of the registration of said preoperative model with an image of a target anatomical structure exposed during surgery.

14 Claims, 8 Drawing Sheets

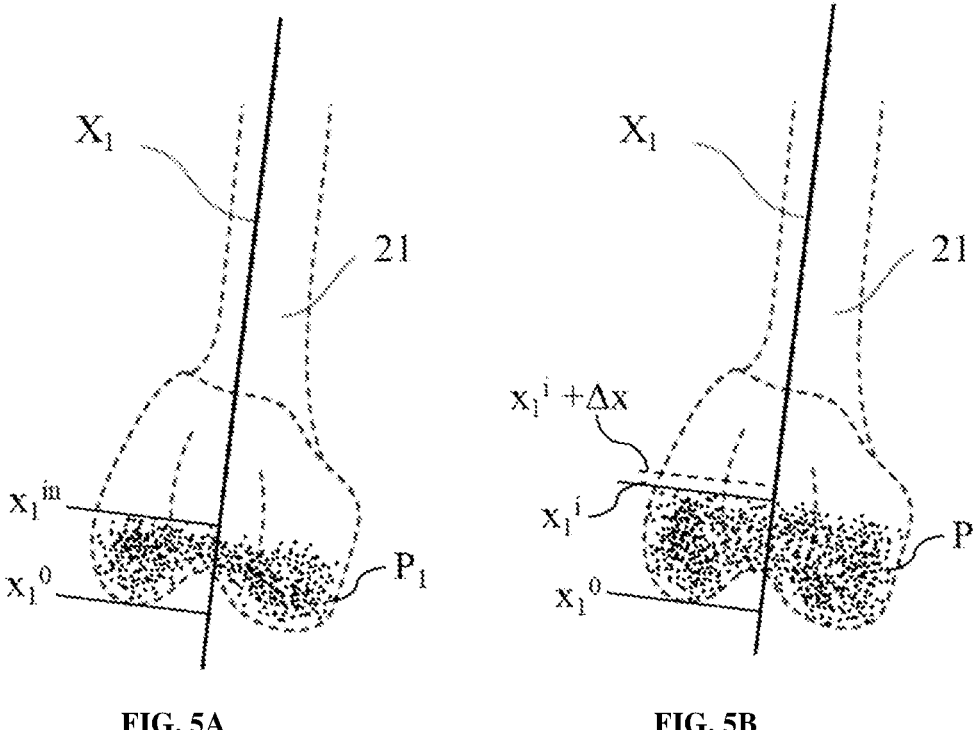
FIG. 5A                    FIG. 5B

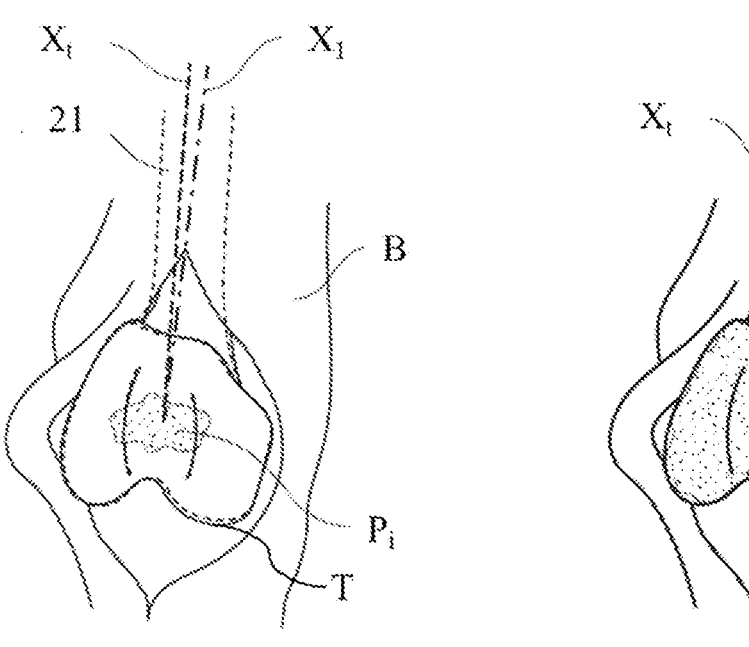
FIG. 6A                    FIG. 6B
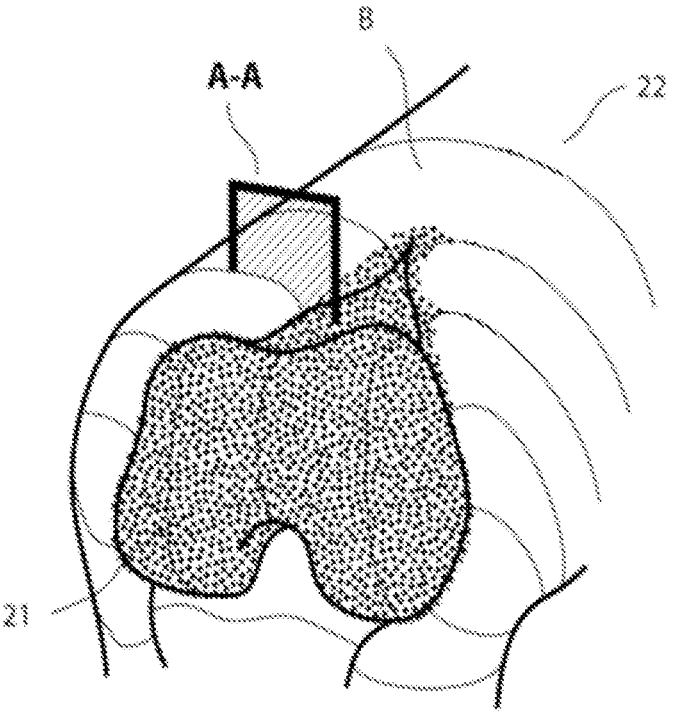
FIG.7A

METHOD AND DEVICE FOR SEGMENTATION AND REGISTRATION OF AN ANATOMICAL STRUCTURE

FIELD OF INVENTION

The present invention relates to the field of image analysis in the medical domain. Notably, the present invention pertains to the analysis of images comprising a target anatomical structure acquired during surgery in order to allow registration of a preoperative model of said target anatomical structure to the images.

BACKGROUND OF INVENTION

Nowadays, computer and robotic assisted surgery is evolving thanks to the improvement achieved by the use of computer methods and robotic devices to plan and execute surgical interventions. The registration of different referential (i.e., coordinate frames), often obtained through the matching of three-dimensional (3D) data sets, represents a fundamental step for the correct connection of surgery planning and surgery execution.

For orthopedic surgery, a number of methods have already been developed that includes registration routines using fiducial markers surgically implanted, generally directly onto the bone of the patient. The replacement of this invasive routine with procedures not needing fiducials for registration is a crucial step towards the minimization of surgical invasiveness.

The registration process allows to compute the transformations linking different coordinate frames. Registration consists in the matching of spatial data sets defined in different coordinate frames.

Registration algorithms in the biomedical application have been proposed to match a preoperative model of an anatomical structure to a data set obtained by an imaging system during the surgery. The preoperative model comprises a set of data points defining a 3D model of the anatomical target structure on which the surgical operation will be performed. It is built before the surgery takes place, based on medical images acquired prior to the operation, such as CT scans, MRI, PET, etc. However, this model does not include any soft-tissue or artificial structures around the anatomy that could be present during the surgery, and this can impact the accuracy of the registration. The present invention provides a solution to filter the preoperative model in order to obtain an optimal registration of a preoperative model of the target anatomical structure during surgery in a known coordinated frame in the surgical theater.

SUMMARY

This invention thus relates to a device for segmentation of a preoperative model of a target anatomical structure in view of a registration of said preoperative model with an image of the target anatomical structure exposed during surgery, said device comprising:

at least one input configured to receive:

at least one 3D image acquired from at least one 3D imaging sensor; said data points of the 3D image representing at least one exposed portion of the target anatomical structure;

the preoperative model comprising data points defined in a model referential having at least one first axis, at least one processor configured to:

initially registering at least one portion of the preoperative model to at least one portion of the 3D image;

define a current sub-set of data points comprising data points from the preoperative model;

generate an intermediate sub-set of data points of the preoperative model comprising the data points of the current sub-set of data points and, in addition, comprising at least one group of additional data points of the preoperative model located along the first axis and outside of the portion of the preoperative model corresponding to the current sub-set of data points;

calculating a distance measure representative of a distance between a respective data point of the intermediate sub-set of data points and a corresponding data point of the 3D image;

determining whether the distance measure is less than a predefined threshold; and in response to determining that the distance measure is less than the predefined threshold, including the respective data point of the intermediate sub-set of data points into the new iteration sub-set;

in response to determining that the distance measure is greater than the predefined threshold, discarding the respective data point of the intermediate sub-set of data points from the new iteration sub-set;

register the preoperative model to at least one portion of the 3D image based on the new iteration sub-set;

repeat, the generation of an intermediate sub-set of data points, calculation of the distance measure, determination and inclusion of data points as the new iteration sub-set, and registration, where the new iteration sub-set is used as the current sub-set of data points, until an exit criterion has been satisfied.

In other words, the preoperative model of the patient's target anatomical structure is iteratively filtered to reduce noise and improve the registration accuracy. For instance, the target anatomical structure may be a bone structure and the noise is caused by the presence of tissues on the bone structure that hinder the registration process.

Advantageously, the present invention allows, through multiple iterations comprising registration of selected subsets of data points of the preoperative model onto the 3D image of the surgical target, to obtain an optimally selected sub-set of data points of the preoperative model wherein the points are associated to the points in the surgical field represented in the 3D image that represent the surgical target. In other words, through the iterations, the sub-set of data points selected from the preoperative model is enriched by adding new points corresponding to data points in the 3D image belonging to the target structure, while the points corresponding to surrounding tissues or artificial structures are filtered out.

Although not limited thereto, the implant of knee prostheses, specially TKA, using robotic assistance or surgical navigation is among the procedures which would mainly benefit from the approach proposed by the present invention. Indeed, in computer and robot assisted TKA the registration step is an important link between the planning and the execution phases, since achievement of the same high geometric accuracy planned during preoperative planning in the actual surgical execution is extremely important.

Alternatively, the invention may also be used on multiple occasions where a registration step is required during surgery. The surgery may be carried out on any anatomical structure such as a joint structure or a bone structure. For example, on a shoulder, a hip, an elbow, an ankle, a tibia etc.

According to one embodiment, the device further comprises at least one output adapted to provide the preoperative model registered to the at least one corresponding portion of the 3D image obtained when the exit criterion is satisfied. The registration of the preoperative model to the 3D image of the surgical field allows to estimate the transformation that aligns the model referential to the target referential in the surgical theater. Since the preoperative surgical planning is previously defined in the model referential, knowing this transformation (i.e., the registration) allows to transpose the actions planned in the preoperative surgical planning into the surgical theater. This is of great interest notably when robotic arms are used to perform the surgery. Furthermore, the use of the preoperative model of the bone and its registration to at least one 3D image of the target in the surgical field allows to know the transformation between the model referential and a target referential independently from any external marker attached to the patient.

According to one embodiment, the target anatomical structure has an elongated shape and the first axis in the model referential is aligned to a longitudinal axis of the preoperative model.

According to one embodiment, the initial sub-set of data points of the model is composed of data points from the preoperative model being comprised between an origin coordinate and a predefined initial iteration coordinate along the first axis, so that the maximum coordinate value along the first axis among the data points of said current sub-set of data points is equal to the predefined initial iteration coordinate.

According to one embodiment, at each iteration the intermediate sub-set of data points of the preoperative model is generated from data points of the current sub-set of data points and, in addition, from at least one group of data points of the preoperative model located between the maximum coordinate value along the first axis among the data points of the current sub-set of data points and said maximum coordinate value plus an iteration step along the first axis.

According to one embodiment, the iteration step is predefined and constant. According to one embodiment, the iteration step is adapted at each iteration.

According to one embodiment, the at least one processor is configured to select the predefined initial iteration coordinate on the base of information concerning the target anatomical structure and/or a type of surgery.

According to one embodiment, the at least one processor is further configured to calculate a registration score representative of the accuracy of the registration between the preoperative model of the target anatomical structure and the current sub-set of data points; and wherein the exit criterion is satisfied when the registration score has reached an optimum value. This advantageously, allows to stop the iterations when the quality of the registration is considered satisfactory. Indeed, the quality of registration is directly 20 linked to the precision of positioning of the surgical tool that is used to operate the target anatomical structure, therefore the more accurate is the registration the more accurate will be the positioning of the surgical tool according to the preoperative surgical planning. Since the target anatomical structure involved in the surgery is firmly secured to the operating table and therefore rigid with respect to the outer environment (i.e., imaging sensor, robotic device, etc.), the registration method of the present invention can be performed only once. The registration process may be repeated in case the target anatomical structure is displaced during the surgery.

According to one embodiment, the registration score is a function of the square root of the average squared distance between the data points of the current sub-set of data points and the corresponding data points in the 3D image. According to one embodiment, the distance measure used in the RMSE computation is the Euclidean distance.

According to one embodiment, the at least one processor is further configured to calculate a registration score representative of the accuracy of the registration between the current sub-set of data points and the corresponding data points in the 3D image; and to use the current sub-set of data points for which the optimum value of the registration score is obtained to register the preoperative model so as to obtain an optimal registration of the preoperative model to the target anatomical structure. Alternatively, the processor may be configured to select the registration result for which the highest registration score has been obtained during the iterations.

According to one embodiment, the exit criterion is configured to stop the iterations when, for a given number of iterations, no data point of the current sub-set of data points is associated to a distance from corresponding data points in the 3D image inferior to the predefined threshold.

According to one embodiment, the at least one processor is further configured to generate the preoperative model of said target anatomical structure by segmentation of medical images comprising at least one portion of said target anatomical structure.

According to one embodiment, the at least one processor is configured to stop the repetition of the generation of an intermediate sub-set of data points, calculation of the distance measure, determination and inclusion of data points as the new iteration sub-set, and registration when the maximum coordinate value along the first axis for all the points of the current sub-set of data points exceeds a predefined final coordinate.

According to one embodiment, the predefined final coordinate is defined on the base of information concerning the target anatomical structure and/or a type of surgery.

The present invention also relates to a computer-implemented method for segmentation of a preoperative model of a target anatomical structure in view of a registration of said preoperative model with an image of a target anatomical structure exposed during surgery, said method comprising:

receiving at least one 3D image acquired from at least one 3D imaging sensor, said data points of the 3D image representing at least one exposed portion of the target anatomical structure of the patient; receiving the preoperative model comprising data points defined in a model referential having at least one first axis, initially registering at least one portion of the preoperative model to at least one portion of the 3D image;

define a current sub-set of data points comprising data points from the preoperative model;

generate an intermediate sub-set of data points of the preoperative model comprising the data points of the current sub-set of data points and, in addition, comprising at least one group of additional data points of the preoperative model located along the first axis and outside of the portion of the preoperative model corresponding to the current sub-set of data points;

calculating a distance measure representative of a distance between a respective data point of the intermediate sub-set of data points and a corresponding data point of the 3D image;

determining whether the distance measure is less than a predefined threshold; and

in response to determining that the distance measure is less than the predefined threshold, including the respective data point of the intermediate sub-set of data points into the new iteration sub-set;

in response to determining that the distance measure is greater than the predefined threshold, discarding the respective data point of the intermediate sub-set of data points from the new iteration sub-set and all future iteration sub-sets;

register the preoperative model to at least one portion of the 3D image based on the new iteration sub-set;

repeat, the generation of an intermediate sub-set of data points, calculation of the distance measure, determination and inclusion of data points as the new iteration sub-set, and registration, where the new iteration sub-set is used as the current sub-set of data points, until an exit criterion has been satisfied.

In addition, the disclosure relates to a computer program comprising software code adapted to perform a method for segmentation of an exposed target anatomical structure compliant with any of the above execution modes when the program is executed by a processor.

The present disclosure further pertains to a non-transitory program storage device, readable by a computer, tangibly embodying a program of instructions executable by the computer to perform a method for segmentation of an exposed target anatomical structure, compliant with the present disclosure.

Such a non-transitory program storage device can be, without limitation, an electronic, magnetic, optical, electromagnetic, infrared, or semiconductor device, or any suitable combination of the foregoing. It is to be appreciated that the following, while providing more specific examples, is merely an illustrative and not exhaustive listing as readily appreciated by one of ordinary skill in the art: a portable computer diskette, a hard disk, a ROM, an EPROM (Erasable Programmable ROM) or a Flash memory, a portable CD-ROM (Compact-Disc ROM).

Definitions

In the present invention, the following terms have the following meanings:

The terms "adapted" and "configured" are used in the present disclosure as broadly encompassing initial configuration, later adaptation or complementation of the present device, or any combination thereof alike, whether effected through material or software means (including firmware).

The term "processor" should not be construed to be restricted to hardware capable of executing software, and refers in a general way to a processing device, which can for example include a computer, a microprocessor, an integrated circuit, or a programmable logic device (PLD). The processor may also encompass one or more Graphics Processing Units (GPU), whether exploited for computer graphics and image processing or other functions. Additionally, the instructions and/or data enabling to perform associated and/or resulting functionalities may be stored on any processor-readable medium such as, e.g., an integrated circuit, a hard disk, a CD (Compact Disc), an optical disc such as a DVD (Digital Versatile Disc), a RAM (Random-Access Memory) or a ROM (Read-Only Memory). Instructions may be notably stored in hardware, software, firmware or in any combination thereof.

"Preoperative model" refers to a three-dimensional digital (or virtual) model being a virtual object in 3 dimensions. The position and orientation of the model is known in the associated model referential.

"Preoperative planning" in the context of surgery, refers to a list of actions to be performed during the different surgical phases. This surgical planning may be obtained by means of a simulation program carried out before the operation which uses radiological images from the anatomical structures of the patient that are the target of the surgery. In the case of a knee arthroplasty operation, for example, pre-operative planning will consist of defining each of the cutting planes and drilling axes in relation to a three-dimensional model of the femur and tibia.

"Referential" refers to a coordinate system that uses one or more numbers, or coordinates, to uniquely determine the position of the points or other geometric elements on a manifold such as Euclidean space.

"(Image) registration" refers to the process of transforming different sets of data into one coordinate system. Image registration involves spatially transforming the "moving" image(s) to align with the "target" image. The reference frame (i.e.; referential) in the target image is stationary, while the other datasets are transformed to match to the target.

BRIEF DESCRIPTION OF THE DRAWINGS

FIG. 5A shows a schematic representation of the first sub-set data of points selected from the preoperative model;

FIG. 5B shows a sub-set of data points selected from the preoperative model for the $i^{th}$ iteration.

FIG. 6A shows a first sub-set of data points of the 3D image, defined at a first iteration of method, registered to the 3D preoperative model.

FIG. 6B shows the sub-set of data points of FIG. 6A, obtained after multiple iterations of the method, registered to the 3D preoperative model.

FIG. 7A shows a schematic prospective view of the point cloud of the preoperative model registered onto the target anatomical structure represented in the 3D image, whose elements are here schematically represented as lines and contours

7

Figure 1:
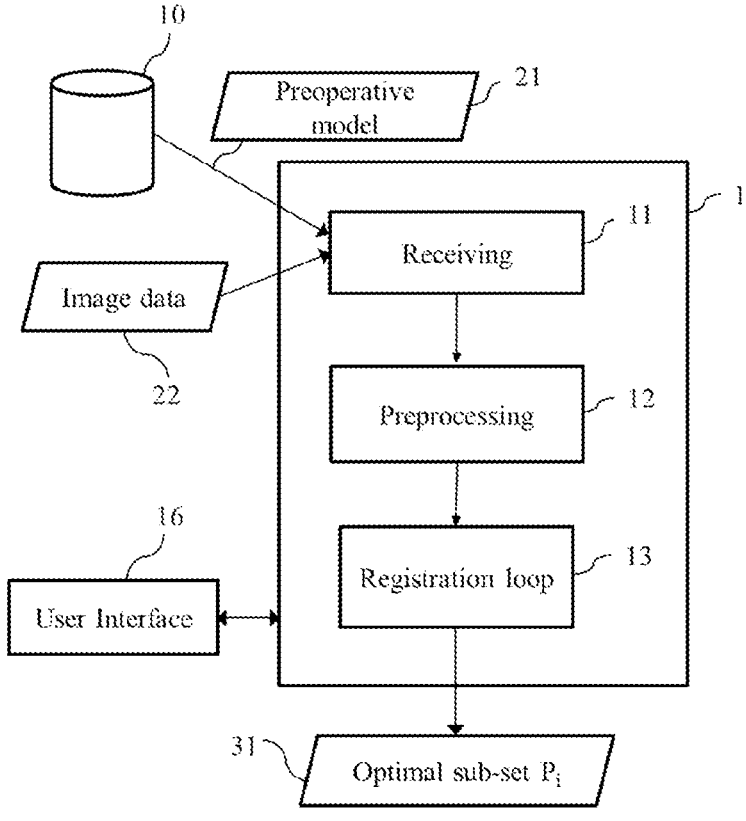
FIG. 1 is a block diagram representing schematically a particular mode of a device for segmentation compliant with the present disclosure.
Figure 8:
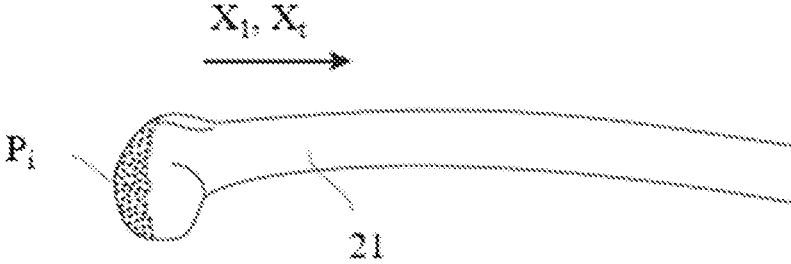
Figure 9:
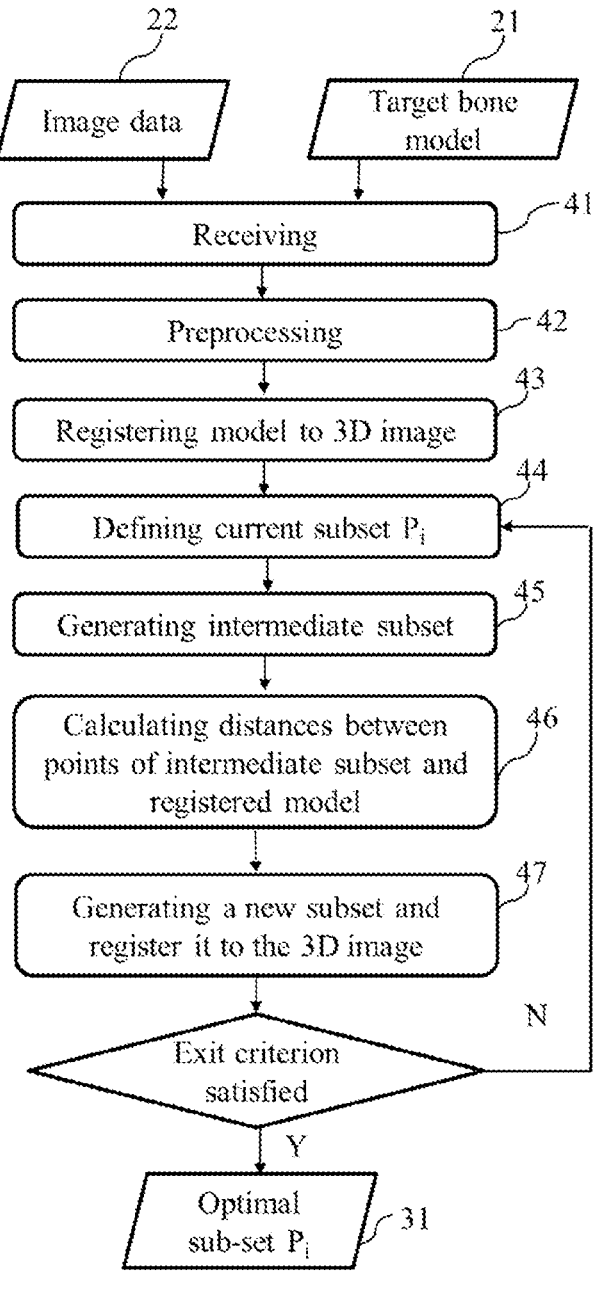
Figure 10:
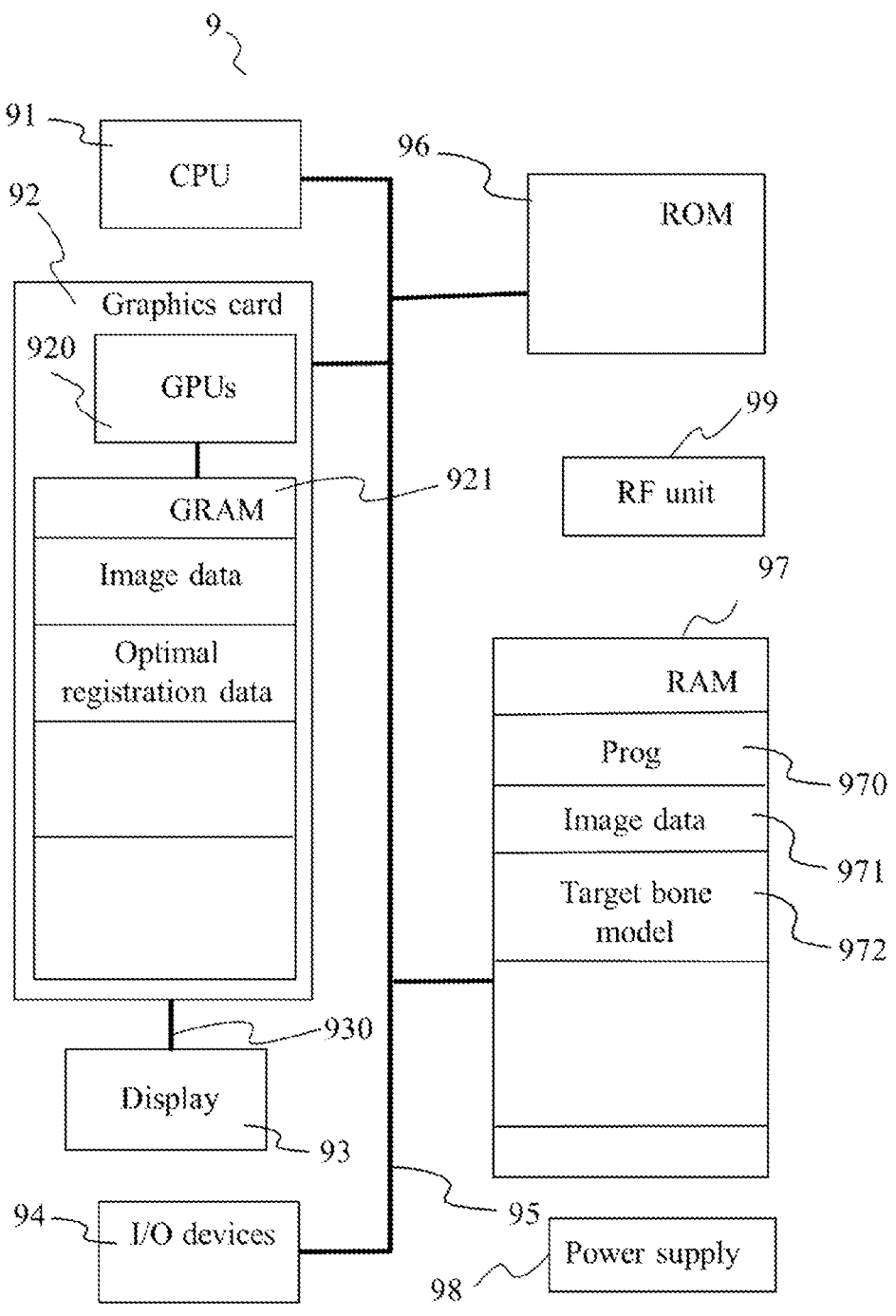

FIG. 8 shows a prospective view of one sub-set of data points of the 3D image registered to the 3D preoperative model;

FIG. 9 is a flow chart showing successive steps executed with the device for predicting of FIG. 1;

FIG. 10 diagrammatically shows an apparatus integrating the functions of the device for segmenting of FIG. 1.

On the figures, the drawings are not to scale, and identical or similar elements are designated by the same references.

DETAILED DESCRIPTION

The present description illustrates the principles of the present disclosure. It will thus be appreciated that those skilled in the art will be able to devise various arrangements that, although not explicitly described or shown herein, embody the principles of the disclosure and are included within its scope.

All examples and conditional language recited herein are intended for educational purposes to aid the reader in understanding the principles of the disclosure and the concepts contributed by the inventor to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Thus, for example, it will be appreciated by those skilled in the art that the block diagrams presented herein may represent conceptual views of illustrative circuitry embodying the principles of the disclosure. Similarly, it will be appreciated that any flow charts, flow diagrams, and the like represent various processes which may be substantially represented in computer readable media and so executed by a computer or processor, whether or not such computer or processor is explicitly shown.

The functions of the various elements shown in the figures may be provided through the use of dedicated hardware as well as hardware capable of executing software in association with appropriate software. When provided by a processor, the functions may be provided by a single dedicated processor, a single shared processor, or a plurality of individual processors, some of which may be shared.

It should be understood that the elements shown in the figures may be implemented in various forms of hardware, software or combinations thereof. Preferably, these elements are implemented in a combination of hardware and software on one or more appropriately programmed general-purpose devices, which may include a processor, memory and input/output interfaces.

The present disclosure will be described in reference to a particular functional embodiment of a device 1 to identify optimal sub-sets of points for segmentation of an exposed target anatomical structure, as illustrated on FIG. 1.

The device 1 is adapted to produce such optimal sub-set of data points 31 for the registration of the preoperative model 21 to the image data 22 representative of at least one 3D image of the target anatomical structure T acquired during surgery. Notably, the optimal sub-set of data points 31 obtained as output comprises mainly the points of one intraoperative model 21 that are associated to the target anatomical structure T, as all points belonging to others structures (i.e., soft tissues like tendons, cartilages, skin etc. or external objects as bone screws, surgical tools, etc.) had been excluded during the multiple iteration of the method.

The 3D image 22 may be derived from at least one 3D imaging sensor present in the surgical theater and positioned in such a way to comprise in its field of view at least a portion of the surgical field comprising the target anatomical structure T. Indeed, during an orthopedic surgery, the surgeon proceeds to the exposure of the target anatomical structure, which in this case may be a bone, on which surgical operations, such as for example, machining or drilling have to be performed. The surgical field, which is basically the region of the patient on which the surgery is to be performed, will comprise the exposed target anatomical structure T and the surrounding structures B such as tissues (i.e., cartilages, tendons, muscles, skin, or a bone which is not targeted during the surgery, and the like) and/or artificial structures (i.e., bone screw, surgical tools, grasping tools etc.). A schematic representation of an exemplary surgical field is provided in FIG. 4(*b*).

The 3D imaging sensor refers to a sensor for acquiring topological data of a real scene in 3 dimensions. These topological data are recorded in the form of a point cloud, and/or a depth map. Herein after the term "data points" will be used to refer both to the point clouds or depth maps, as the person skilled in the art knows how to perform registration on both point clouds or depth maps. Therefore, at least one portion of the data points of one 3D image 22 represents at least one exposed portion of the target anatomical structure T of the patient. The other data points are generally associated to the structures B surrounding the target anatomical structure T comprised in the field of view of the 3D imaging sensor.

Multiple acquisition techniques may be utilized to obtain these topological data for example techniques based on the measure of wave propagation time such as ultrasound or light (LIDAR, Time-of-Flight) or stereoscopic camera or sensor, which is a type of camera with two or more lenses with a separate image sensor or film frame for each lens. This allows the camera to simulate human binocular vision, and therefore gives it the ability to capture three-dimensional images. Other techniques may be based on light deformation, such as structured-light 3D scanners which project a pattern of light on an object and look at the deformation of the pattern on the object. The advantage of structured-light 3D scanners is speed and precision. Instead of scanning one point at a time, structured light scanners scan multiple points or the entire field of view at once. Scanning an entire field of view in a fraction of a second reduces or eliminates the problem of distortion from motion. Another class of techniques is based on laser scanning for sampling or scanning a surface using laser technology, such as hand-held laser or time-of-flight 3D laser scanner. More in general, any techniques known by the skilled artisan providing topological data of a real scene in 3 dimensions may be used for the implementation of the present invention.

The 3D image(s) 22 may be grayscale images, or color (RGB-D) images among others. The 3D image(s) 22 may include numerical data, such as digital data. Those data may include individual image data in a compressed form, as well known to a person skilled in image compression, such as e.g. in compliance with e.g. in compliance with JPEG (for Joint Photographic Experts Group), JPEG 2000 or HEIF (for High Efficiency Image File Format) standard.

As the 3D image(s) 22 is (are) acquired by the 3D imaging sensor, the data points of the 3D images are associated to a sensor referential, notably the referential of the 3D imaging sensor.

For a given registration running, the 3D image(s) 22 may be derived from a unique 3D imaging sensor used to acquire at least one 3D image of at least a portion of the surgical field comprising the target anatomical structure T. Alternatively, the 3D image(s) 22 may be derived from two or more 3D imaging sensors, or even from two or more different kinds of 3D imaging sensors. In this case, data from multiple sensors could be combined into a single fused point cloud or depth map.

The preoperative model 21 comprises a set of data points defining a 3D model of the anatomical target structure on which the surgical operation will be performed. The data points of the preoperative model 21 are defined in a model referential wherein a first axis $X_1$ is defined. The preoperative model 21 may be derived from medical images acquired prior to the operation. Generally, said medical images are images (or slices) of the patient obtained by medical imaging (CT, MRI, PET, etc.). The 3D preoperative model 21 may be obtained by a segmentation treatment of these medical images, followed by an interpolation between the images. The 3D preoperative model 21 obtained from segmentation and interpolation of medical images may be modified to take into account elements that are not visible in the medical images, for example cartilage that is not visible in CT scan images. In this case, the modifications may be generated from training data or biomechanical simulation data. The 3D preoperative model 21 may also be generated from statistical models or abacuses and patient data associated or not with the preoperative medical images. In addition, the preoperative model 21 may be adapted taking into account data acquired during the operation. Alternatively, the 3D preoperative model 21 may be generated through the digitization of 3D points on the exposed bone surface using an optical tracking system (for example 3D imaging sensor itself or another system present in the surgical theater).

Though the presently described device 1 is versatile and provided with several functions that can be carried out alternatively or in any cumulative way, other implementations within the scope of the present disclosure include devices having only parts of the present functionalities.

The device 1 is advantageously an apparatus, or a physical part of an apparatus, designed, configured and/or adapted for performing the mentioned functions and produce the mentioned effects or results. In alternative implementations, the device 1 is embodied as a set of apparatus or physical parts of apparatus, whether grouped in a same machine or in different, possibly remote, machines. The device 1 may for example have functions distributed over a cloud infrastructure and be available to users as a cloud-based service, or have remote functions accessible through an API.

In what follows, the modules are to be understood as functional entities rather than material, physically distinct, components. They can consequently be embodied either as grouped together in a same tangible and concrete component, or distributed into several such components. Also, each of those modules is possibly itself shared between at least two physical components. In addition, the modules are implemented in hardware, software, firmware, or any mixed form thereof as well. They are preferably embodied within at least one processor of the device 1.

As shown in FIG. 1, the device 1 comprises a module 11 for receiving the image data 22 (i.e., 3D image(s)) and the preoperative model 21, which may be stored in one or more local or remote database(s) 10. The latter can take the form of storage resources available from any kind of appropriate storage means, which can be notably a RAM or an EEPROM (Electrically-Erasable Programmable Read-Only Memory) such as a Flash memory, possibly within an SSD (Solid-State Disk). In advantageous embodiments, the preoperative model 21 have been previously generated by a system including the device for generating the 3D preoperative models. Alternatively, the preoperative model 21 are received from a communication network.

The device 1 further comprises optionally a module 12 for preprocessing the received 3D image(s) 22 and possibly the preoperative model 21. The module 12 may notably be adapted to standardize the received image data 22 for sake of efficiency and reliable processing. It may transform the image data 22, e.g., by image or video decompression. According to various configurations, the module 12 is adapted to execute only part or all of the above functions, in any possible combination, in any manner suited to the following processing stage.

In advantageous modes, the module 12 is configured for preprocessing the image data 22 so as to have the images standardized. This may enhance the efficiency of the downstream processing by the device 1. Such a standardization may be particularly useful when exploiting images originating from different sources, including possibly different imaging systems.

The device 1 comprises a module 13 whose general purpose is that of advantageously filter out the data points of the preoperative model 21 so as to leave only the data points that are associated to exposed target anatomical structure in the 3D image 22 and remove data points associated, in the 3D image 22, to soft tissues or surgical tools. More in details, the module 13 is configured for iteratively performing a succession of operations, notably comprising registration of different sub-sets of data points of the preoperative model 21 to the associated data points in the 3D image 22, till a predefined exit criterion is met.

As the target anatomical structure T may have an elongated shape, such as a long bone, the first axis $X_1$ may be defined so as to be aligned to a longitudinal axis $X_l$ of said target anatomical structure in the model referential, as shown in FIG. 4(*a*). In general, the axis $X_1$ equation (i.e., spatial orientation and position in the model referential) may be defined on the base of predefined information concerning the type of target surgical structure, the type of surgery to be performed, a preference of the surgeon and the like. Said first axis may be defined to pass through at least one portion of the preoperative model 21 which corresponds to a portion of the target anatomical structure T that is exposed during the surgery. The first axis $X_1$ may have been previously defined by a device that has generated the preoperative model 21, in which case the equation of the first axis $X_1$ is received by the receiving module 11 alongside to the data points of the preoperative model 21. Alternatively, the module 13 may be configured to define the first axis $X_1$.

Figure 2:
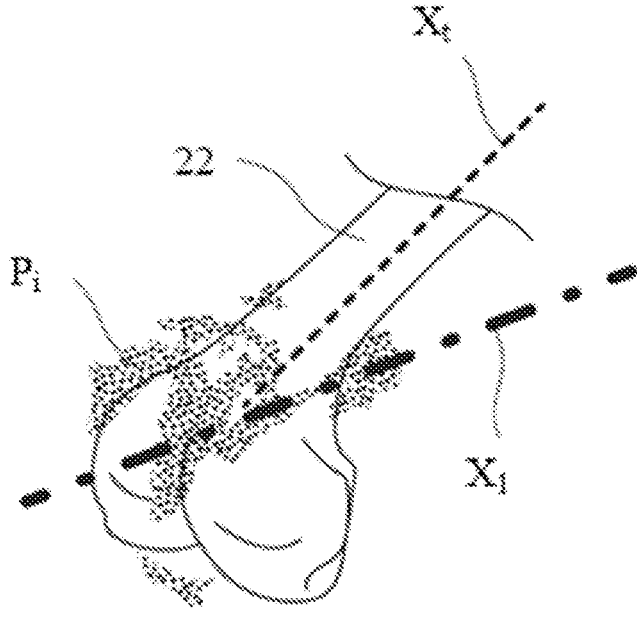
FIG. 2 is a schematic representation of at least one sub-set of data points of the 3D image and the preoperative model after initial registration, before filtering out the data points not related to the target anatomical structure, according with the present disclosure.
Figure 3:
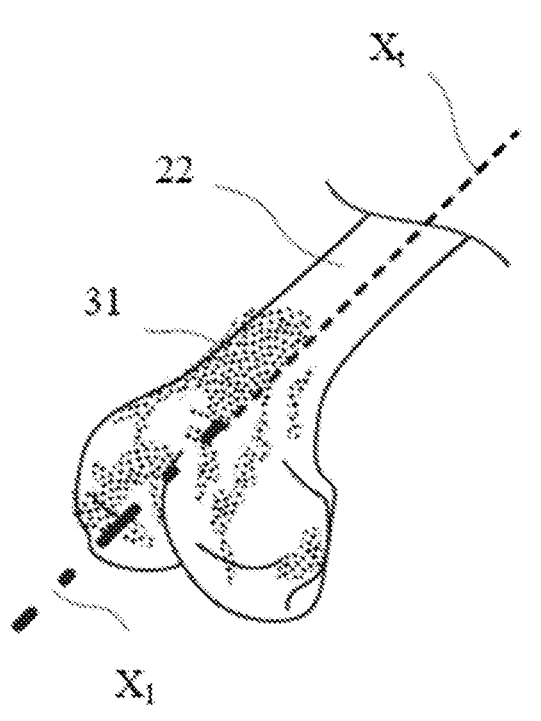
FIG. 3 is a schematic representation of the preoperative model registered to the optimal sub-set of data points of the 3D image according with the present disclosure.

More in detail, the module 13 is configured to perform initialization steps, which may be performed only once for each 3D image 22 received. The first initialization step comprises registering at least one portion of the data points of the preoperative model 21 to at least one portion of the data points of the 3D image 22. FIG. 2 shows an example of the result of this first registration of the preoperative model 21 to at least one portion of data points of the 3D image 22. In this example, the target anatomical structure is a femur. In this case, the preoperative model 21 is not registered in an optimal way as it can be noticed from the fact that the model's longitudinal axis (i.e., first axis $X_1$) and the longitudinal axis $X_t$ of the femur in the 3D image 22 are not overlapped (i.e., the two axes do not pass through a same couple of points). On the other hand, FIG. 3 shows the overlapping obtained from the registration of the preoperative model 21 and the optimal sub-set of data points 31 obtained as a result of the iterations performed in module 13. In this case, as the outlier data points are absent or really few in the optimal sub-set of data points 31, the registration is particularly accurate and the preoperative model's longitudinal axis $X_1$ and the longitudinal axis of the femur $X_t$ in the 3D image 22 are overlapped. The steps implemented by module 13 leading to this result will be explained in details in the following paragraphs.

After said first registration, the module 13 is configured to perform the second initialization step on the preoperative model 21 received in the device 1. Said second initialization step consists in the selection of first sub-set of data points $P_1$ of the registered preoperative model 21. The points of the sub-set of data points $P_1$ are selected from the data points of the registered 3D preoperative model 21 so that each selected point is related to at least one portion of the target anatomical structure, which is exposed during the surgery, and not to other surrounding structures.

Figures 4A, 4B, 4C:
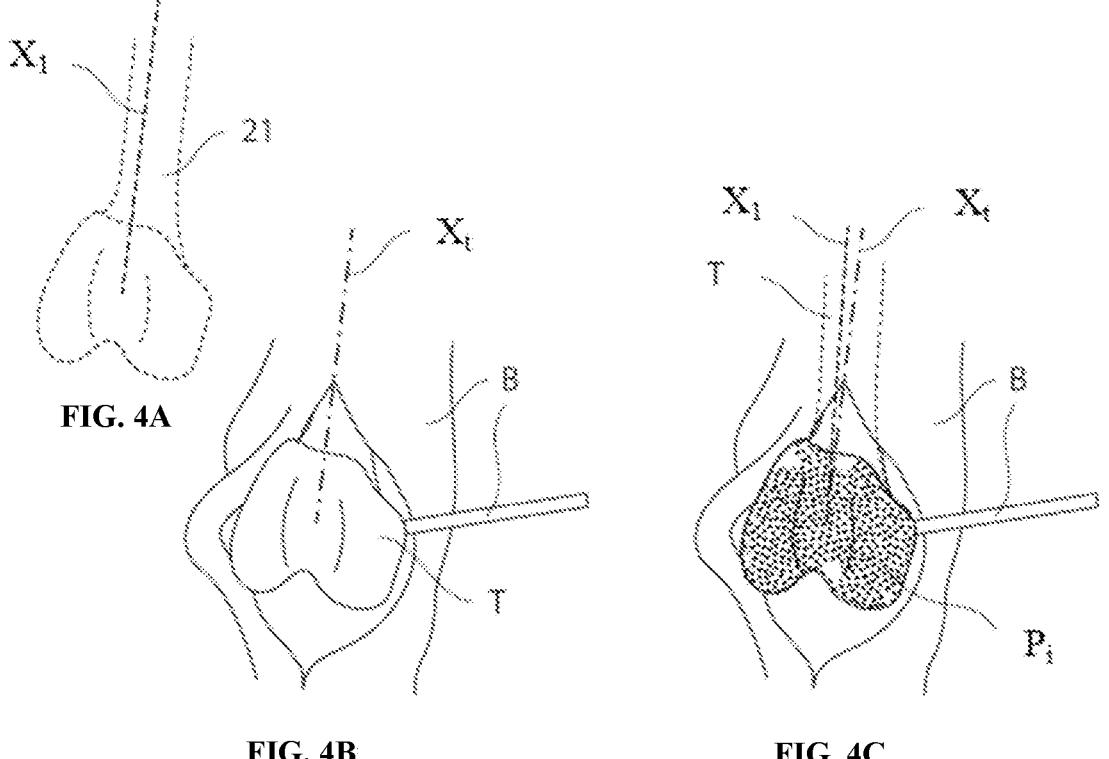
FIG. 4A a schematic representation of the 3D preoperative model of the target anatomical structure.
FIG. 4B shows a schematic representation of the surgical field comprising the exposed target anatomical structure.
FIG. 4C shows a schematic representation of a sub-set of data points of the preoperative model overlapped of schematic representation of the surgical field.

FIG. 4A shows the preoperative model of a long bone having a longitudinal axis $X_1$, FIG. 4B shows a schematic representation of the surgical field, comprising the target anatomical structure T and the surrounding tissues/objects B, which is represented in the 3D image 22 (as it would be seen by the human eye or a color camera for example). FIG. 4C shows a schematic representation of the preliminary registration of a sub-set of data points of the preoperative model 21 on the 3D image 22 (comprising both target and non-target anatomical structures). Due to the fact that the 3D image 22 comprises data points also associated to structures not represented in the preoperative model 21, the result of the registration is poor and therefore the longitudinal axis of the target structure $X_t$ is not overlapped nor even aligned with the longitudinal axis of the model (i.e., $X_1$ in this example with a long bone), as shown in FIG. 4(c).

In order to select data points of the registered preoperative model 21 relating in majority to the at least one exposed portion of the target anatomical structure for the first sub-set of data points $P_1$, the module 13 may be configured to select data points of the preoperative model 21 comprised between two coordinates defined along the first axis $X_1$. In one example, illustrated in FIG. 5(a), the two coordinates used for the definition of first sub-set of data points $P_1$ are an origin coordinate x) and a predefined initial iteration coordinate $x_1^{in}$ along the first axis $X_1$. Therefore, for this first sub-set of data points $P_1$, the maximum coordinate value $x_1^1$ along the first axis $X_1$ among their data points is equal to the predefined initial iteration coordinate $x_1^{in}$.

According to one embodiment, the predefined initial iteration coordinate $x_1^{in}$ is selected on the base of information concerning the target anatomical structure and/or the type of surgery. The initial iteration coordinate $x_1^{in}$ may be advantageously chosen as the central point of a bone which is typically exposed at the moment of the surgery. For example, said central point may be the femur knee center of tibia knee center, which are typically exposed during a total knee arthroplasty. According to a second example, the central point may be a scapula glenoid center for a shoulder arthroplasty procedure. In other examples, the invention could be applied to any other target anatomical structure on which a surgery is to be subsequently performed.

The operations necessary to define the first sub-set of data points $P_1$ do not need to be repeated any more in the iterations that are performed by module 13. The sub-set of data points undergoing the $i^{th}$ iteration is called in the present disclosure current sub-set of data points $P_i$. Therefore, the sub-set of data points $P_1$ is considered as the current sub-set of data point for the first iteration performed by module 13.

Given a newly defined current sub-set of data points $P_i$, the module 13 is configured to perform at least one first, second, third, fourth and fifth operation that are iteratively repeated until the exit criterion has been satisfied.

The first operation may comprise the generation of an intermediate sub-set of data points $P_i^{int}$ obtained by adding to the data points of the sub-set of data points $P_i$ at least one point or a group of data points from the data points of the registered preoperative model 21.

Notably, the intermediate sub-set of data points of the preoperative model may be generated by adding, to the data points of the current sub-set of data points $P_i$, at least one group of additional data points of the preoperative model 21 located along the first axis and outside of the portion of the preoperative model 21 corresponding to the current sub-set of data points $P_i$.

According to one example represented in FIG. 5, the data points to be added to the intermediate sub-set of data points $P_i^{int}$ are selected as the data points of the preoperative model 21 located between the maximum coordinate value x-along the first axis $X_1$ and said maximum coordinate value plus an iteration step $\Delta x$ (i.e., $x_1^i + \Delta x$), again along the first axis $X_1$, as illustrated in FIG. 5(b). Since all data points of the registered preoperative model 21 comprised between $x_1^i$ and $x_1^i + \Delta x$ are added, these data points may correspond to data points of the 3D image 22 relating to the target anatomical structure T or to a surrounding tissue/structure B.

The iteration step $\Delta x$ may be predefined and constant, or alternatively it may be predefined and decreasing from one iteration to the following. Indeed, while moving further from the origin coordinate $x_1^0$, it is expected that the number of points added to the intermediate sub-set of data points are more and more associated to data points of the 3D image 22 that do not relate to the target anatomical structure T but to the surrounding tissues/structures B.

Alternatively, the iteration step $\Delta x$ may be predefined and constant, or alternatively it may be predefined and increasing from one iteration to the following. This embodiment, advantageously allow to increase the speed of calculation.

In one alternative embodiment, the iteration step $\Delta x$ is adapted at each iteration on the base of the registration score $s_{i-1}$ calculated during the previous iteration (i.e., when the module 13 is configured to calculate the registration score). The length of the step $\Delta x$ is inversely proportional to the registration score $s_{i-1}$. Alternatively, the iteration step $\Delta x$ may be dependent from the current position along the principal axis $x_1^i$ or be scaled on the base of the current iteration value i. The iteration step $\Delta x$ may be as well configured to be shorter in proximity of the origin coordinate $x_1^0$ and as well in close proximity to the coordinate along the first axis wherein there is no more exposed bone, but only soft tissues (i.e., end of the surgical incision exposing the bone).

Figure 7B:
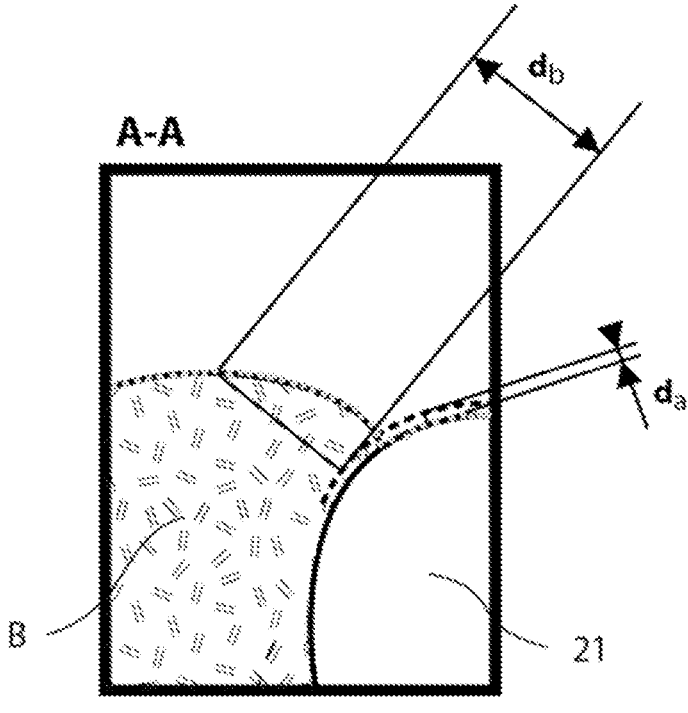
FIG. 7B shows the cross-section corresponding to the plane A-A represented in FIG. 7A, wherein the grey points represent the points of the 3D image belonging to the plane A-A and the black segments represent the points of the preoperative model image belonging to the plane A-A.

The second operation is configured to calculate a distance measure between each data point of the intermediate sub-set of data points $P_i^{int}$ and the corresponding points in the 3D image 22. The module 13 may use an Euclidean distance, a L2 norm, a Manhattan distance, or any appropriate distance measure known by the person skilled in the art. FIGS. 7A and 7B provide an illustration of the distance measure calculation. FIG. 7A provides a prospective view of an intermediate sub-set of data points registered to the 3D image 22 (for an iteration i of the present method), the 3D image 22 representing both soft tissues B and the target anatomical structure T comprised in the surgical scene. In this representation, the soft tissues B and the target anatomical structure T represented in the 3D image 22 (i.e., point cloud) are represented by solid lines contours to simplify the graphical representation with the overlapped data points of the intermediate sub-set of data points. FIG. 7B shows the cross-section view of a plane A-A represented as well in FIG. 7A. In the cross-section A-A, the solid lines provide a representation of the contours of the soft tissues B and the target anatomical structure T that are present in the surgical scene, the grey dots represent the data points of 3D image 22 which lie in the A-A plane and the black segments represent the data points of the intermediate sub-set of data points $P_i$ which lie as well in the A-A plane. FIG. 7B graphically shows that the distance da calculated between one data point of the intermediate sub-set of data points and the corresponding data points of 3D image 22 is particularly small when both data points are associated to the target anatomical structure T. Inversely, the distance $d_b$ calculated between one data point of the intermediate subset of data points (i.e., associated to the target anatomical structure T, as it is one data point selected from the preoperative model 21) and the corresponding data points of 3D image 22 is wider, when the corresponding data point on the 3D image 22 is associated to soft tissue B still covering the target anatomical structure T. Therefore, discarding the data points in the intermediate sub-set of data points that have distance greater than a predefined threshold efficiently allows to remove from the intermediate sub-set of data points all data points associated to the data points in the 3D image representing soft tissues or surgical tools. This second operation may as well comprise comparing the distance measures for each data point of the intermediate sub-set of data points $P_i^{int}$ to a predefined threshold.

Then the third operation is configured to generate a new sub-set of data points. The new sub-set of data points $P_{i+1}$ is generated so as to comprise the data points of the intermediate sub-set of data points $P_i^{int}$ having a distance from the registered preoperative model 21 inferior to a predefined threshold. This operation advantageously allows to remove all the outlier data points from the preoperative model that are not associated to data points of the 3D images relating to the target anatomical structure T which may had been added to the intermediate sub-set of data points $P_i^{int}$ during the first operation. In this way, all data points representing soft tissues on top of the target anatomical structure or artificial structures, such as the head of a bone screw protruding from the target anatomical structure, will be deleted from the intermediate sub-set of data points pint.

More precisely, this third operation comprises the step of determining whether the distance measure is less than a predefined threshold. In response to determining that the distance measure is less than the predefined threshold, the respective data point of the intermediate sub-set of data points is added to the new iteration sub-set $P_{i+1}$. In the other case, in response to determining that the distance measure is greater than the predefined threshold, the respective data point of the intermediate sub-set of data points is discarded from the new iteration sub-set $P_{i+1}$. The data points discarded from the new iteration sub-set $P_{i+1}$ will be therefore absent also from all future iterations sub-sets, as the new iteration sub-set $P_{i+1}$ is used as current sub-set of data points for the next iteration i+1 if the exit criterion is not yet satisfied.

The module 13 is configured to perform the fourth operation configured to register the new iteration sub-set $P_{i+1}$ selected from the preoperative model 21 to the corresponding portion of the 3D image 22.

FIGS. 6A and 6B provide a graphical representation of the evolution of the current sub-set of data points and the accuracy of the registration of the preoperative model after multiple iterations. On FIG. 6A is indeed represented an example of first sub-set of data points $P_1$ comprising a smaller amount of data points all associated to 3D image data points relating to the target anatomical structure. However, since the preoperative model 21 is registered for the first time (i.e., during the first initialization step) using data points which may also correspond to data points in the image 22 not relating to the exposed target anatomical structure T, the registration is still of poor quality as shown by the fact that the axis $X_1$ and $X_t$ are not overlapping. FIG. 6B shows the result of adding at each iteration to the sub-set of data points only the data points of the registered preoperative model associated to data points of the 3D image 22 corresponding to the target anatomical model T and not the surrounding tissues B, thanks to the selection of the data points based of their distances from the registered model. The surrounding tissues B are represented in the present figures only to help in the understanding of the invention. The surrounding tissues B are not part of the preoperative model 21, and in FIGS. 6A-6B, the data points selected and represented are mainly associated to the target anatomical structure T. FIG. 8 shows a prospective view of the preoperative model 21 registered to a current sub-set of data points $P_i$.

Optionally, the module 13 is configured to calculate, for the $i^{th}$ iteration, a registration score $s_i$ representative of the accuracy of the registration between the new sub-set of data points $P_{i+1}$ and the corresponding data point in the 3D image 22. The registration score $s_i$ may be obtained as a function of a square root of the average squared differences (Root Mean Squared Error RMSE) of the 3D distances between the points of the new sub-set of data points $P_{i+1}$ and the corresponding data point in the 3D image 22. The registration score $s_i$ may be obtained as a function of the Euclidian distance between corresponding data points pairs in both new sub-set of data points $P_{i+1}$ or between known anatomical landmarks comprised in the new sub-set of data points $P_{i+1}$ and the corresponding data points in the 3D image 22.

Finally, the module 13 is configured to perform the fifth operation configured to verify if the predefined exit criterion has been satisfied.

According to one embodiment, the predefined exit criterion is based on the evaluation of the value of the registration score $s_i$. For example, the iterations may be stopped when the registration score $s_i$ has exceeded a threshold or reached an optimum value.

According to an alternative embodiment, the exit criterion is configured to stop the iterations when, during a given number of iterations (i.e., one, two or more iterations), no pair of corresponding data points in the intermediate sub-set of data points and 3D image 22 is associated to a distance inferior to the predefined threshold. The exit criterion may be configured as well to stop if less than a predefined number of data points of the intermediate sub-set of data points of the model has a distance from the corresponding data points in the 3D image inferior to the predefined threshold.

According to one embodiment, the exit criterion is configured to stop the iteration of the first, second, third and fourth operation when the maximum coordinate value $x_1^i$ along the first axis $X_1$ for all the points of the new sub-set of data points $P_{i+1}$ exceeds a predefined final coordinate $x_1^{max}$. The predefined final coordinate $x_1^{max}$ may be defined on the base of information concerning the target anatomical structure and/or a type of surgery. Alternatively, the exit criterion may be imposed as a predefined maximum number of iterations, so that the iteration stops when this predefined maximum number $i_{max}$ is reached.

Whenever the exit criterion is not satisfied, the module 13 is configured to start a new iteration i+1 using the new sub-set of data points $P_{i+1}$, which is the current sub-set of data points for the iteration i+1. Therefore, during the new iteration i+1, the module 13 is configured to repeat on the new sub-set of data points $P_{i+1}$ the first, second, third, fourth and fifth operation described above. Inversely, when the exit criterion is satisfied, the module 13 is configured to stop the iterations (i.e., stop repeating the first, second, third, fourth and fifth operation).

Therefore, the present device 1 advantageously allows to obtain an optimal registration 32 of the preoperative model 21 to the exposed target anatomical structure T represented in the 3D image 22. The optimal registration is obtained using the optimal sub-set of data points of the preoperative model 21 selected through the iterations that satisfies the chosen exit criterion. The optimal sub-set of data points may be the one selected during the last iteration performed before satisfaction of the exit criterion or one of the sub-set of data points for which the best registration score or other evaluation parameter is obtained.

FIG. 6B shows the overlapping of the preoperative model 21 on top of the target anatomical structure T represented in the 3D image 22 that is obtained when the optimal sub-set of data points of the preoperative model is registered to the corresponding data points of the 3D image 22 belonging to the target anatomical structure T. In this case, the outlier data points are absent or really few in the optimal sub-set of data points, therefore the registration is particularly accurate and the model's longitudinal axis $X_1$ and the target anatomical structure axis $X_t$ are overlapped.

According to one embodiment, the device 1 further comprises a modelling module (not represented), configured to generate the preoperative model of said target anatomical structure 21 by segmentation of medical images comprising at least one portion of said target anatomical structure T. Said medical images may be images acquired prior to the operation, such as images obtained from CT, MRI, PET, etc. the modulization module may be configured to perform segmentation of the target anatomical structure T on these images and then interpolation between segmented images.

The device 1 is interacting with a user interface 16, via which information can be entered and retrieved by a user. The user interface 16 includes any means appropriate for entering or retrieving data, information or instructions, notably visual, tactile and/or audio capacities that can encompass any or several of the following means as well known by a person skilled in the art: a screen, a keyboard, a trackball, a touchpad, a touchscreen, a loudspeaker, a voice recognition system.

In its automatic actions, the device 1 may for example execute the following process (FIG. 9):

receiving the preoperative model and the image data 22 (step 41), preprocessing the image data 22 with a view for a more efficient and/or reliable processing (step 42), registering the preoperative model 21 to at least one portion of the 3D image 22 (first initialization step Δ3);

carrying out an iterative loop on the preoperative model data point 21 until an exit criterion is satisfied (steps 44 to 47), notably:

defining a current sub-set of data points $P_i$ of the model (step 44);

generate an intermediate sub-set of data points of the preoperative model comprising the data points of the current sub-set $P_i$ and, in addition, comprising at least one group of additional data points of the preoperative model 21 (step 45);

calculating a distance measure representative of a distance between a respective data point of the intermediate sub-set of data points and a corresponding data point of the 3D image 22 (step 46);

generating a new iteration sub-set of data points $P_{i+1}$ comprising the data points of the intermediate sub-set having a distance from the corresponding point in the 3D image inferior to a predefined threshold, and registering the new iteration sub-set of data points $P_{i+1}$ to the 3D image (step 47); and outputting the registered model 31.

The process of FIG. 10 may as well comprise a step of registering the preoperative model 21 using the optimal sub-set of data points (i.e., current sub-set of data points for which the optimal registration score has been obtained) to the corresponding data points in the 3D image 22.

A particular apparatus 9, visible on FIG. 9, is embodying the device 1 described above. It corresponds for example to a workstation, a laptop, a tablet, a smartphone, or a head-mounted display (HMD).

That apparatus 9 is suited for segmentation of 3D images and registration of a model of an exposed target anatomical structure on the 3D images. It comprises the following elements, connected to each other by a bus 95 of addresses and data that also transports a clock signal:

a microprocessor 91 (or CPU);

a graphics card 92 comprising several Graphical Processing Units (or GPUs) 920 and a Graphical Random Access Memory (GRAM) 921; the GPUs are quite suited to image processing, due to their highly parallel structure;

a non-volatile memory of ROM type 96;

a RAM 97;

one or several I/O (Input/Output) devices 94 such as for example a keyboard, a mouse, a trackball, a webcam; other modes for introduction of commands such as for example vocal recognition are also possible;

a power source 98; and a radiofrequency unit 99.

According to a variant, the power supply 98 is external to the apparatus 9.

The apparatus 9 also comprises a display device 93 of display screen type directly connected to the graphics card 92 to display synthesized images calculated and composed in the graphics card. The use of a dedicated bus to connect the display device 93 to the graphics card 92 offers the advantage of having much greater data transmission bitrates and thus reducing the latency time for the displaying of images composed by the graphics card. According to a variant, a display device is external to apparatus 9 and is connected thereto by a cable or wirelessly for transmitting the display signals. The apparatus 9, for example through the graphics card 92, comprises an interface for transmission or connection adapted to transmit a display signal to an external display means such as for example an LCD or plasma screen or a video-projector. In this respect, the RF unit 99 can be used for wireless transmissions.

It is noted that the word "register" used hereinafter in the description of memories 97 and 921 can designate in each of the memories mentioned, a memory zone of low capacity (some binary data) as well as a memory zone of large capacity (enabling a whole program to be stored or all or part of the data representative of data calculated or to be displayed). Also, the registers represented for the RAM 97 and the GRAM 921 can be arranged and constituted in any manner, and each of them does not necessarily correspond to adjacent memory locations and can be distributed otherwise (which covers notably the situation in which one register includes several smaller registers).

When switched-on, the microprocessor 91 loads and executes the instructions of the program contained in the RAM 97.

As will be understood by a skilled person, the presence of the graphics card 92 is not mandatory and can be replaced with entire CPU processing and/or simpler visualization implementations.

In variant modes, the apparatus 9 may include only the functionalities of the device 1. In addition, the device 1 may be implemented differently than a standalone software, and an apparatus or set of apparatus comprising only parts of the apparatus 9 may be exploited through an API call or via a cloud interface.

The invention claimed is:

1. A device for segmentation of a preoperative model of a target anatomical structure in view of a registration of said preoperative model with an image of a target anatomical structure exposed during surgery, said device comprising:

at least one input configured to receive:

at least one 3D image acquired from at least one 3D imaging sensor, the 3D image comprising data points representing at least one exposed portion of the target anatomical structure;

the preoperative model comprising data points defined in a model referential having at least one first axis, at least one central processing unit configured to:

initially registering at least one portion of the preoperative model to at least one portion of the 3D image;

define a current sub-set of data points comprising data points from the preoperative model;

generate an intermediate sub-set of data points of the preoperative model comprising the data points of the current sub-set of data points and, in addition, comprising at least one group of additional data points of the preoperative model located along the first axis and outside of the portion of the preoperative model corresponding to the current sub-set of data points;

calculating a distance measure representative of a distance between a respective data point of the intermediate sub-set of data points and a corresponding data point of the 3D image;

determining whether the distance measure is less than a predefined threshold; and in response to determining that the distance measure is less than the predefined threshold, including the respective data point of the intermediate sub-set of data points into the new iteration sub-set;

in response to determining that the distance measure is greater than the predefined threshold, discarding the respective data point of the intermediate sub-set of data points from the new iteration sub-set;

register the preoperative model to at least one portion of the 3D image based on the new iteration sub-set;

repeat, the generation of an intermediate sub-set of data points, calculation of the distance measure, determination and inclusion of data points as the new iteration sub-set, and registration, where the new iteration sub-set is used as the current sub-set of data points until an exit criterion has been satisfied.

2. The device according to claim 1, wherein the target anatomical structure has an elongated shape and the first axis in the model referential is aligned to a longitudinal axis of the preoperative model.

3. The device according to claim 1, where the initial sub-set of data points of the model is composed of data points from the preoperative model being comprised between an origin coordinate and a predefined initial iteration coordinate along the first axis, so that the maximum coordinate value along the first axis among the data points of said current sub-set of data points is equal to the predefined initial iteration coordinate.

4. The device according to claim 3, where at each iteration the intermediate sub-set of data points of the preoperative model is generated from data points of the current sub-set of data points and, in addition, from at least one group of data points of the preoperative model located between the maximum coordinate value along the first axis among the data points of the current sub-set of data points and said maximum coordinate value plus an iteration step along the first axis.

5. The device according to claim 1, wherein the iteration step is predefined and constant, or adapted at each iteration.

6. The device according to claim 1, wherein the at least one central processing unit is configured to select the predefined initial iteration coordinate on the base of information concerning the target anatomical structure and/or a type of surgery.

7. The device according to claim 1, wherein the at least one central processing unit is further configured to calculate a registration score representative of the accuracy of the registration between the preoperative model of the target anatomical structure and the current sub-set of data points; and wherein the exit criterion is satisfied when the registration score has reached an optimum value.

8. The device according to claim 7, wherein the registration score is a function of the square root of the average squared distances between the data points of the current sub-set of data points and the corresponding data points in the 3D image.

9. The device according to claim 1, wherein the exit criterion is configured to stop the iterations when for a given number of iterations no data point of the current sub-set of data points is associated to a distance from corresponding data points in the 3D image inferior to the predefined threshold.

10. The device according to claim 1, wherein the at least one central processing unit is further configured to generate the preoperative model of said target anatomical structure by segmentation of medical images comprising at least one portion of said target anatomical structure.

11. The device according to claim 1, wherein the at least one central processing unit is configured to stop the repetition of the generation of an intermediate sub-set of data points, calculation of the distance measure, determination and inclusion of data points as the new iteration sub-set, and registration, when the maximum coordinate value along the first axis for all the points of the current sub-set of data points exceeds a predefined final coordinate.

12. The device according to claim 11, wherein the predefined final coordinate is defined on the base of information concerning the target anatomical structure and/or a type of surgery.

13. A computer-implemented method for segmentation of a preoperative model of a target anatomical structure in view of a registration of said preoperative model with an image of a target anatomical structure exposed during surgery, said method comprising:

receiving at least one 3D image acquired from at least one 3D imaging sensor, the 3D image comprising data points representing at least one exposed portion of the target anatomical structure of the patient;

receiving the preoperative model comprising data points defined in a model referential having at least one first axis;

initially registering at least one portion of the preoperative model to at least one portion of the 3D image;

define a current sub-set of data points comprising data points from the preoperative model;

generate an intermediate sub-set of data points of the preoperative model comprising the data points of the current sub-set of data points and, in addition, comprising at least one group of additional data points of the preoperative model located along the first axis and outside of the portion of the preoperative model corresponding to the current sub-set of data points;

calculating a distance measure representative of a distance between a respective data point of the intermediate sub-set of data points and a corresponding data point of the 3D image;

determining whether the distance measure is less than a predefined threshold; and in response to determining that the distance measure is less than the predefined threshold, including the respective data point of the intermediate sub-set of data points into the new iteration sub-set;

in response to determining that the distance measure is greater than the predefined threshold, discarding the respective data point of the intermediate sub-set of data points from the new iteration sub-set;

register the preoperative model to at least one portion of the 3D image based on the new iteration sub-set;

repeat, the generation of an intermediate sub-set of data points, calculation of the distance measure, determination and inclusion of data points as the new iteration sub-set, and registration, where the new iteration sub-set is used as the current sub-set of data points, until an exit criterion has been satisfied.

14. A non-transitory computer readable medium comprising instructions which, when executed by a computer, cause the computer to carry out the method according to claim 13.

* * * * *